United States Patent
Gatto

(10) Patent No.: US 6,852,680 B2
(45) Date of Patent: Feb. 8, 2005

(54) DITHIOCARBAMATES CONTAINING ALKYLTHIO AND HYDROXY SUBSTITUENTS

(75) Inventor: Vincent James Gatto, Midlothian, VA (US)

(73) Assignee: Ethyl Corporation, Richmond, VA (US)

( * ) Notice: Subject to any disclaimer, the term of this patent is extended or adjusted under 35 U.S.C. 154(b) by 519 days.

(21) Appl. No.: 10/062,161

(22) Filed: Oct. 26, 2001

(65) Prior Publication Data

US 2003/0139301 A1 Jul. 24, 2003

(51) Int. Cl.[7] ..................... C10M 135/18; C07C 333/20
(52) U.S. Cl. ................. 508/444; 508/254; 508/563; 508/569; 508/570; 508/572; 508/584; 558/239; 252/78.1
(58) Field of Search ........................... 508/444; 558/239

(56) References Cited

U.S. PATENT DOCUMENTS

| | | | |
|---|---|---|---|
| 2,710,872 A | 6/1955 | Thompson | |
| 3,356,702 A | 12/1967 | Farmer | |
| 3,407,222 A | 10/1968 | Lies | |
| 3,509,051 A | 4/1970 | Farmer | |
| 3,867,359 A | 2/1975 | Beadle | |
| 4,098,705 A | 7/1978 | Sakurai | |
| 4,125,479 A | 11/1978 | Chesluk | |
| 4,758,362 A | 7/1988 | Butke | |
| 4,836,942 A | 6/1989 | Lam | |
| 4,876,375 A | 10/1989 | Lam | |
| 4,885,365 A | 12/1989 | Lam | |
| 4,927,552 A | 5/1990 | Lam | |
| 4,931,576 A | 6/1990 | Wirth et al. | |
| 4,957,643 A | 9/1990 | Lam | |
| 5,618,778 A | 4/1997 | Wirth | |
| 5,629,272 A | 5/1997 | Nakazato | |
| 5,674,820 A | 10/1997 | Manks | |
| 5,686,397 A | 11/1997 | Baranski | |
| 5,693,598 A | 12/1997 | Abraham | |
| 5,698,498 A | * 12/1997 | Luciani et al. | .............. 508/193 |
| 5,705,458 A | 1/1998 | Roby | |
| 5,789,357 A | 8/1998 | Baranski | |
| 5,840,664 A | 11/1998 | Karol | |
| 5,902,776 A | 5/1999 | Dohner | |

FOREIGN PATENT DOCUMENTS

| | | |
|---|---|---|
| EP | 0 349 131 A2 | 1/1990 |
| EP | 1 006 173 A1 | 7/2000 |
| FR | 2 735 130 A1 | 12/1996 |
| WO | WO 09963028 A1 | 12/1999 |

OTHER PUBLICATIONS

Smalheer et al "Lubricant Additives", Section I–Chemistry of Additives, pp. 1–11, 1967.*
Len, Christophe et al, "Synthesis and Antifungal Activity of Novel Bis(dithiocarbamate) Derivatives of Glycerol," J. Agric. Food Chem. 1996, pp. 2856–2858, vol. 44, XP–002228721.
Latyuk, I. et al, "1–Alkylthiopropanol–2–derivatives as multifunctional additives to lubricating oils," Database CAPLUS 'Onlinel, Chemical Abstracts Service, Columbus Ohio, US, Neftekhimiya, vol. 42, No. 2, 2002, XP–002228722, Abstract Only.
Kubota, S. et al, "Synthesis and biological activity of 1,3–dithiol, 1,2–dithiolane and 1,3–dithiane–2–thione (abstract)," Database CAPLUS 'Online!, Chemical Abstracts Service, Columbus, Ohio, US, Journal of the Faculty of Agriculture, Kyushu University, vol. 22, No. 1–2, 1977, XP–002228723, Abstract Only.
Zh. Org. Khim. (1991), 27(1), 161–170.
Zh. Org. Khim (1988), 24(2), 286–291.
Zh. Org. Khim (1985), 21(6), 1173–1176.
Neftekhim (1983), 23(3), 409–412.
Neftepererab. Neftekhim. (Moscow) (1983), (1), 20–22.

* cited by examiner

Primary Examiner—Ellen M. McAvoy
(74) Attorney, Agent, or Firm—Dennis H. Rainear; Leah Oubre Robinson

(57) ABSTRACT

This invention relates to a low cost, wear inhibitor containing novel dithiocarbamates with alkylthio and hydroxy substituents that can be used to formulate low phosphorus lubricants. In addition to wear inhibition, the dithiocarbamate compositions of the invention provide substantial oxidation protection to lubricating oils and are not detrimental to fuel economy.

67 Claims, No Drawings

DITHIOCARBAMATES CONTAINING ALKYLTHIO AND HYDROXY SUBSTITUENTS

FIELD OF THE INVENTION

This invention relates to a low cost wear inhibitor that can be used to formulate low phosphorus lubricants. In addition to wear inhibition, the new inhibitors provide substantial oxidation protection and are not detrimental to fuel economy.

BACKGROUND OF THE INVENTION

Studies have suggested that emissions systems can be deactivated as a result of contamination from compounds derived from the engine oil. Other studies have suggested that emissions system durability may be improved by using lubricants containing high metal/phosphorus ratios. Reducing the level of phosphorus in the engine oils has also been suggested as a means of prolonging the efficiency of the catalytic converter. The phosphorus in engine oils originates primarily from zinc dialkyldithiophosphates (ZDDP's), which are used to prevent wear and control oxidation. Over the years ZDDP's have demonstrated reliable anti-wear and antioxidant effectiveness. Most engine builders would not recommend engine oils which contain substantial reductions from today's ZDDP levels without extensive proof in the laboratory and the field that wear protection is acceptable. Commercial engine oils meeting API SJ requirements usually contain approximately 0.10 wt. % phosphorus derived from ZDDP. A substantial reduction in ZDDP's, which may be required for catalytic converter durability, would result in significantly higher engine wear and oil oxidation. To compensate for the use of less ZDDP in engine oils, supplemental wear and oxidation inhibitors are required.

Dithiocarbamates have been known in the art for some time. Examples of various structurally different dithiocarbamates are disclosed in the following patents:

| | | | | |
|---|---|---|---|---|
| 3,407,222 | 5,693,598 | 4,885,365 | 4,125,479 | 5,902,776 |
| 3,867,359 | 5,686,397 | 4,836,942 | 4,758,362 | 3,509,051 |
| 2,710,872 | 5,789,357 | 4,927,552 | 5,629,272 | 3,356,702 |
| 5,840,664 | 4,957,643 | 4,876,375 | 5,759,965 | 4,098,705 |

All patents, patent applications, and articles or publications are incorporated herein by reference for their full disclosure.

Examples of alkoxy- and hydroxyl-substituted dithiocarbamates are known in the art and examples are disclosed in the following references: Zh. Org. Khim. (1991), 27(1), 161–170; Zh. Org. Khim. (1988), 24(2), 286–291; Z. Chem. (1987), 27(1), 24–25; Zh. Org. Khim. (1985), 21(6), 1173–1176; Neftekhim (1983), 23(3), 409–412; and Neftepererab. Neftekhim. (Moscow) (1983), (1), 20–22.

Methods of producing alkylglycidyl thioethers are reported in U.S. Pat. Nos. 4,931,576 and 5,618,778.

Examples of commercially available dithiocarbamates include Vanlube 7723, a methylenebis (dibutyldithiocarbamate), Molyvan A, a molybdenum oxysulfide dithiocarbamate, Molyvan 822, an organo molybdenum dithiocarbamate, Vanlube AZ, a zinc diamyldithiocarbamate, Vanlube 71, a lead diamyldithiocarbamate, Vanlube 73, an antimony dialkyldithiocarbamate, and Vanlube 732, a dithiocarbamate derivative, all obtained from R.T. Vanderbilt Company, Inc.

SUMMARY OF THE INVENTION

According to an embodiment of the present invention, novel dithiocarbamate compositions are prepared by reacting alkyl glycidyl thioethers with primary and/or secondary amines and carbon disulfide. These new dithiocarbamates are effective antioxidants and wear inhibitors and can be used in low phosphorus lubricants as a partial replacement for ZDDP. An additional benefit of the dithiocarbamates of the present invention is that they are not detrimental to the friction modification properties of lubricants.

The compounds described in this invention act to improve wear and oxidation performance in engine oils containing reduced levels of ZDDP's, i.e. engine oils containing reduced levels of phosphorus.

A further benefit which these low cost wear inhibitors of the present invention provide is to reduce friction in fully formulated crankcase engine oils containing low levels of ZDDP's, thereby, providing improved fuel economy to the engine.

This invention describes a new class of alkylthio- and hydroxyl-substituted dithiocarbamate compounds that have utility as anti-wear and oxidation inhibitors in, for example, crankcase oils. The dithiocarbamates of the present invention may be used in a wide variety of crankcase oils including passenger car engine oils, heavy duty diesel engine oils, railroad oils, and natural gas engine oils. They may be used as the main anti-wear component to deliver wear and oxidation protection in lubricants that contain no additional anti-wear additives. In this case they would be considered the principle anti-wear component. Used as such they can be applied towards the development of zero phosphorus crankcase oils. They may also be used as a supplemental anti-wear component in lubricants containing one or more additional anti-wear additives. An example of this would be their use as supplemental anti-wear components in passenger car engine oils containing reduced levels of phosphorus.

A reduced level of phosphorus for SJ oils is defined as any phosphorus level less than the maximum currently allowable level of 1000 ppm. Typical reduced phosphorus levels may range from about 900 ppm phosphorus to levels as low as about 500 ppm phosphorus or lower. In such cases, the dithiocarbamates of the present invention can be used in combination with ZDDP's to deliver both wear and oxidation performance.

DETAILED DESCRIPTION OF THE INVENTION

The chemical structure of the alkylthio- and hydroxyl-substituted dithiocarbamates according to an embodiment of the present invention is shown below, where R and R' may be hydrogen or alkyl with the requirement that at least one of R and/or R' is alkyl, R" is alkyl or R'''OCOCH$_2$ or R'''OCOCH$_2$CH$_2$ where R''' is alkyl, and X is S. In a preferred embodiment, R" is alkyl with a chain length of C$_4$ to C$_{12}$, more preferably C$_9$ to C$_{12}$.

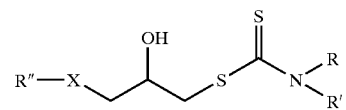

In an embodiment of the present invention, it is preferred that the total sum of carbon atoms in R, R' and R" be greater than ten so that the additive is of low volatility and remains in the formulated crankcase oil at elevated operating temperatures. Additives with ten or less carbons are too volatile for use in the high temperature crankcase environment. In use, such volatile components would evaporate out of the crankcase before they could perform their anti-wear and anti-oxidant functions. According to the present invention, alkyl groups for R, R', R", and R'" may vary from 1 to about 22 carbon atoms and can include all possible linear, or n-, and branched, or iso-, alkyl isomers. Examples of typical alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl and include all possible isomers of each alkyl type. For example, the 2-ethylhexyl alkyl group is considered an isomer of the octyl group. R and R' can be independently selected from alkyl groups having three to eight carbon atoms, and preferably having four to six carbon atoms.

The alkylthio- and hydroxyl-substituted dithiocarbamates of the present invention may be prepared in one embodiment by combining at approximately equal molar concentrations an epoxide, a primary or secondary amine, and carbon disulfide. The reactions are carried out at low temperatures, such as 0° to 30° C., but temperatures as high as, for example, 80° C. are operative herein.

Thus, in another embodiment, the present invention is directed to a method of preparing a composition comprising reacting an alkyl glycidyl thioether with a primary and/or secondary amine, and carbon disulfide.

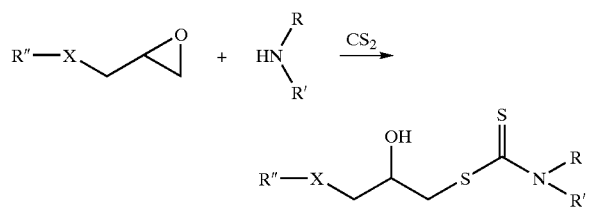

It is preferred that equal molar concentrations of the three components (epoxide, amine, and carbon disulfide) be used. However, a small excess of any one or two components may be used, especially if the excess can be removed once the reaction is complete. For example, a typical molar ratio of epoxide to amine to carbon disulfide may be about 1:1:1.2.

Examples of epoxides that may be used in preparing the additives of the present invention can include methylglycidyl thioether, ethylglycidyl thioether, n-propylglycidyl thioether, n-butylglycidyl thioether, sec-butylglycidyl thioether, n-hexylglycidyl thioether, cyclohexylglycidyl thioether, n-octylglycidyl thioether, tert-nonylglycidyl thioether, n-dodecylglycidyl thioether, tert-dodecylglycidyl thioether, and mixtures of these. Additional epoxides that may be used in the present invention include carboxylic acid ester-substituted alkyl glycidyl thioethers, such as those with the following chemical structures:

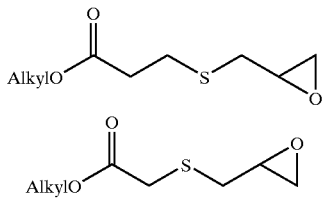

where the alkyl group can vary from methyl to dodecyl and can include both linear and branched alkyl groups.

Methods of producing alkylglycidyl thioethers are reported in U.S. Pat. Nos. 4,931,576 and 5,618,778.

A diluent may be used in the reaction but such diluents are not necessary. In fact, it is preferred that a diluent not be used in order to keep manufacturing costs low and production cycle times short. Examples of diluents include water, alcohols, hydrocarbon solvents, aromatic solvents, chlorinated solvents, polar aprotic solvents, diluent oils, process oils, and base oils. Diluents may be carried over from the preparation of the epoxides and used in the subsequent preparation of the alkylthio- and hydroxyl-substituted dithiocarbamates. For example, in one embodiment of the present invention, the dithiocarbamates may be prepared in two steps by first preparing the epoxide from the mercaptan and epichlorohydrin, without isolation or purification of the epoxide, followed by reaction of the epoxide with the amine and carbon disulfide. In such a case, the water from the preparation of the epoxide is retained and carried over into the reaction to assist in the preparation of the alkylthio- and hydroxyl-substituted dithiocarbamates of the present invention. This reaction, as shown below, allows the preparation of the new dithiocarbamates from readily available raw materials in two reaction steps using only one reactor.

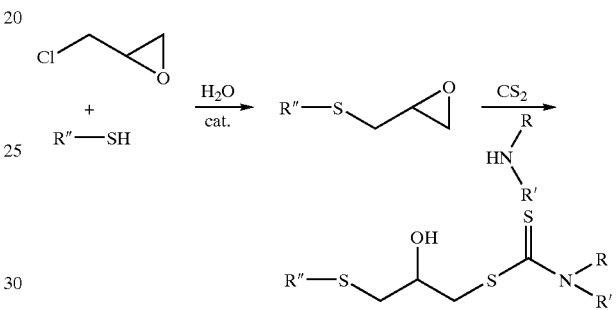

Thus, in another embodiment, the present invention is directed to a method including the steps: providing an epoxide by reacting a mercaptan and epichlorohydrin; and reacting the epoxide with the amine and carbon disulfide. In one embodiment of this method, the epoxide is not isolated or purified before reacting with said amine and carbon disulfide.

A catalyst may be used in the reaction but such catalysts are not necessary. In fact, it is preferred that a catalyst not be used in order to keep manufacturing costs low and production cycle times short.

However, catalysts may be required to improve yields of the alkylthio- and hydroxyl-substituted dithiocarbamates. Examples of catalysts that may be used include the alkali and alkaline earth metal hydroxides such as lithium hydroxide, sodium hydroxide, potassium hydroxide, magnesium hydroxide, and calcium hydroxide. The catalyst may be used as a true catalyst, were the concentration is less than stoichiometric relative to the amine, or it may be used as a reagent, where the concentration is stoichiometric or greater relative to the amine.

The reaction between amines, carbon disulfide and epoxides are exothermic and as such do not require heating. In fact, the combination of the three components will generate substantial heat and usually requires cooling for control and to prevent loss of the volatile carbon disulfide. Reaction temperatures can vary from 0° C. to 30° C. during the combination of the components, and from 20° C. to 80° C. after the component addition.

A typical reaction involves adding, over 1 hour, the amine to a stirred solution containing carbon disulfide and epoxide at a temperature controlled between 0° and 5° C. by the addition rate. After the addition the reaction mixture is heated at 60° to 80° C. for 1 to 2 hours. A vacuum strip may be used to remove excess or residual carbon disulfide or unreacted amine. The vacuum strip is generally performed for 1 to 2 hours at 60° to 80° C. Solvents, if used, may be removed by vacuum distillation. Catalysts, if used, may be removed by carrying out a series of aqueous washes and/or filtrations. Again, it is preferred to carry out these reactions in the absence of solvent and catalysts.

Modifications to the reactions may be made without substantially changing the product produced. For example, trace quantities of hydrogen peroxide may be added to reduce the odor of certain products.

When the alkylthio- and hydroxyl-substituted dithiocarbamates of the present invention are prepared in two steps from the mercaptan, it is possible that small quantities of by-products may form. For example, unreacted epichlorohydrin in the first step may react with two equivalents of amine and two equivalents of carbon disulfide to form a novel product of the type shown below where R and R' are as defined above, and preferably are $C_3$ or greater. For the present invention, this novel by-product is referred to herein as 2-hydroxypropyl-1,3-bis-dialkylcarbamodithioate.

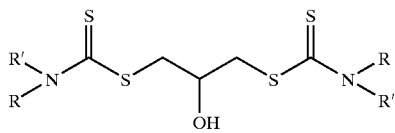

The presence of this compound in small quantities in the product is not detrimental and may in fact be beneficial since it possesses structural features similar to the alkylthio- and hydroxyl-substituted dithiocarbamates. This compound can be eliminated, if desired, by purification of the intermediate epoxide.

A small amount of epichlorohydrin in the first step may react with two equivalents of mercaptan to form a product of the type shown below where R" is as defined above. The presence of this compound in small quantities in the product is not detrimental and may in fact be beneficial since it possesses structural features similar to the alkylthio- and hydroxyl-substituted dithiocarbamates of the present invention. The presence of this compound can be eliminated by purification of the intermediate epoxide.

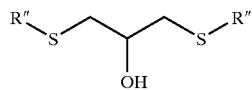

The principle difference between the dithiocarbamates of the prior art and the alkylthio- and hydroxyl-substituted dithiocarbamates of the present invention lies in the presence of two types of sulfur within the same molecule. The prior art dithiocarbamates contain sulfur in the form of the dithiocarbamate functional group. The new dithiocarbamates of this invention contain sulfur in two forms, i.e., as the dithiocarbamate functional group, and as a sulfide functional group. The combination of two forms of sulfur, in which one form is a sulfide and the other form is a dithiocarbamate, combined with the presence of the bridging hydroxyl groups, gives these new dithiocarbamates unique properties as antioxidants and anti-wear inhibitors, while at the same time showing no harm to finished lubricant frictional properties.

Further advantages of the new alkylthio- and hydroxyl-substituted dithiocarbamates are as follows:

They are ashless. This is an advantage in formulating low ash lubricants such as low ash heavy duty diesel engine oils and natural gas engine oils.

They do not contain phosphorus. This is primarily an advantage when formulating low or zero phosphorus lubricants for passenger car engine oils. The use of phosphorus-free additives improves catalytic converter performance, which results in reduced NOx emissions over the life of the passenger car.

They have low thermal stabilities. This improves the performance of the new dithiocarbamates as anti-wear additives. Some commercial dithiocarbamates have very high thermal stabilities and as such are used primarily as anti-oxidants in high temperature applications. An example of such a commercial dithiocarbamate with high thermal stability is methylenebis (dibutyldithiocarbamate).

It has also been found that when X is equal to a group other than S, the performance of lubricating oils containing the resulting dithiocarbamate is significantly diminished. In order to maximize performance of the lubricating oils it is critical to have X=S. This will be demonstrated in the performance bench tests provided in the examples below.

The alkylthio- and hydroxyl-substituted dithiocarbamates of the present invention may be used as antioxidants and anti-wear additives in a wide variety of lubricants. Examples of typical applications include passenger car engine oils, heavy duty diesel engine oils, railroad oils, natural gas engine oils, industrial and automotive gear oils, automatic and manual transmission fluids, hydraulic oils, rust and oxidation oils, turbine oils, and greases. They may also be used in a wide variety of viscosity grade oils and basestock types.

These alkylthio- and hydroxyl-substituted dithiocarbamates can be used to formulate low phosphorus passenger car engine oils by replacing all or part of the ZDDP's currently used. One advantage of these new dithiocarbamates over ZDDP's is that the additives of the present invention are not detrimental to the friction modification properties of the lubricant. This can translate to improved fuel economy performance in certain types of passenger car engines. Another advantage is that they do not contain phosphorus, so there is currently no mandated upper limit on the quantities of such compounds that may be used in passenger car oils.

Thus, the present invention also provides a lubricant additive comprising a novel dialkyl dithiocarbamate of the present invention, as well as lubricating oil containing such a lubricant additive. Lubricating oils of the present invention can further contain at least one of a detergent, a dispersant, an antiwear agent, a friction modifier, a pour point depressant, a foam inhibitor, a corrosion inhibitor, a rust inhibitor, and a viscosity index improver. In addition, the lubricating oils of the present invention can further contain at least one antioxidant selected from diphenylamines, phenothiazines, hindered phenols, alkyl phenols, sulfurized hindered phenols, sulfurized alkyl phenols, methylene-bridged hindered phenols, sulfides and polysulfides, sulfurized olefins, sulfurized fats and sulfurized oils.

The compositions of the present invention are effective for reducing the oxidation of lubricating oils in which the compositions are incorporated. In addition, the compositions of the present invention reduce deposit formation in an engine lubricated with a lubricating oil containing the compositions, relative to the deposits formed in an engine lubricated with an oil which does not contain a composition of the present invention. Also, engine wear and engine friction are reduced by lubricating the engine with an oil containing a dialkyl dithiocarbamate composition of the present invention. Fuel economy, color retention, and odor reduction are also benefits derived from the use of the compositions of the present invention in oils used to lubricate engines, relative to engines lubricated with oils which do not contain the compositions of the present invention. Finally, improved engines, automatic transmissions, turbines, gears, and hydraulics are provided by the present invention when such equipment is lubricated with the compositions and oils of the present invention.

EXAMPLES

Comparative Example 1

A 250 mL four neck round bottom flask is equipped with a magnetic stirrer, an addition funnel, a thermometer, and a nitrogen inlet. A slight positive pressure of nitrogen atmosphere is maintained in the reaction flask. The reactor is charged with 2-ethylhexyl glycidyl ether (28.0 g, 0.150 mol) and carbon disulfide (13.0 g, 0.171 mol). The mixture is stirred with cooling to approximately room temperature (tap water bath). Bis(2-ethylhexyl)amine (35.8 g, 0.148 mol) is slowly added to the reaction over a 1 hour period. An exotherm is observed and the addition is controlled to keep the reaction temperature under 30° C. After 4 hours at ambient temperature the mixture is gently heated for 1 hour at 50° C. The reaction mixture is cooled below 30° C. and an additional charge of carbon disulfide (1.2 g, 0.016 mol) is added. Stirring at ambient temperature is continued overnight. The next morning the reaction is heated to 50° C. and held at that temperature, under vacuum, for 1.5 hours. A yellow viscous liquid (74.7 g, 98.7%) is isolated. Sulfur content=12.41 wt % (theory=12.72 wt %), Nitrogen content=2.94 wt % (theory=2.78 wt %). Low molecular weight GPC analysis of the liquid shows the presence of a single peak (100%, r. t.=22.3 min). FT-IR, $^{13}$C-NMR and H-NMR analysis confirms that the main component of the mixture is 3-(2-ethylhexyloxy)-2-hydroxypropyl bis(2-ethylhexyl)carbamodithioate having the following chemical structure:

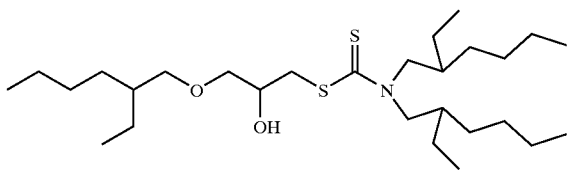

Comparative Example 2

A 250 mL four neck round bottom flask is equipped with a magnetic stirrer, an addition funnel, a thermometer, and a nitrogen inlet. A slight positive pressure of nitrogen atmosphere is maintained in the reaction flask. The reactor is charged with 2-ethylhexyl glycidyl ether (28.0 g, 0.150 m) and carbon disulfide (14.3 g, 0.188 m). The mixture is stirred with cooling to approximately room temperature (tap water bath). Dibutylamine (19.2 g, 0.149 m) is slowly added to the reaction over a 30-minute period. An exotherm is observed and the addition is controlled to keep the reaction temperature under 30° C. After 2 hours at ambient temperature the mixture is gently heated for 2 hours at 35° C. followed by 1 hour at 50° C. Volatile components are removed under vacuum at 50° C. for 1.5 hours. A yellow viscous liquid (57.8 g, 95.7 %) is isolated. Sulfur content=16.07 wt % (theory=16.37 wt %), Nitrogen content=3.86 wt % (theory= 3.58 wt %). Low molecular weight GPC analysis of the liquid shows the presence of predominantly one peak (99%, r. t.=23.0 min). FT-IR, $^{13}$C-NMR and H-NMR analysis confirms that the main component of the mixture is 3-(2-ethylhexyloxy)-2-hydroxypropyl dibutylcarbamodithioate having the following chemical structure:

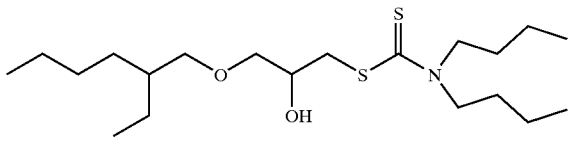

Inventive Example 1

A 1000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (46.3 g, 0.50 mol) and tert-dodecylmercaptan (101.1 g, 0.50 mol). The mixture is stirred with cooling to approximately 5°–10° C. Sodium hydroxide (21.2 g, 0.53 mol), water (230 g) and tetrabutylammonium hydroxide (40% in water, 6.0 g, 6 mmol) are combined with mixing and slowly added to the epichlorohydrin and tert-dodecylmercaptan over a 1 hour period. An exotherm is observed and cooling is continued maintaining the reaction temperature between 5°–10° C. during the addition. After the addition the reaction is heated for 2 hours at 50° C. and cooled to 5° C. Carbon disulfide (40.0 g, 0.53 mol) is then added rapidly to the reaction mixture. Next, dibutylamine (65.0 g, 0.50 mol) is slowly added over 1 hour while maintaining the reaction temperature between 5°–15° C. The reaction is warmed to ambient temperature overnight. The following morning the reaction is heated at 80° C. for 1 hour and then 0.60 g of 30% hydrogen peroxide is added at 70° C. The reaction is heated at 70° C. for an additional 15 minutes, cooled to 50° C., and the phases separated. The organic portion is washed with 2×100 mL of water. The organic solution is returned to a 500 mL three neck round bottom flask and residual water is removed under vacuum at 60° C. for 3 hours. The product is filtered through a coarse fritted glass funnel yielding 220.0 g (94.5%) of a clear yellow viscous liquid with the following physical and chemical properties:

| | |
|---|---|
| Nitrogen Content | 3.14 wt % |
| Sulfur Content | 19.68 wt % |
| Viscosity @ 40° C. | 295 cSt |
| Low Molecular Weight GPC Analysis | 97.1% dialkylated product (r.t. = 22.7 min) |
| TGA Weight Loss | 10% loss @ 212° C. |
| | 25% loss @ 241° C. |
| | 50% loss @ 268° C. |

FT-IR, $^{13}$C-NMR and H-NMR analysis confirms that the main component of the mixture is 3-(tert-dodecylthio)-2- hydroxypropyl dibutylcarbamodithioate having the following chemical structure:

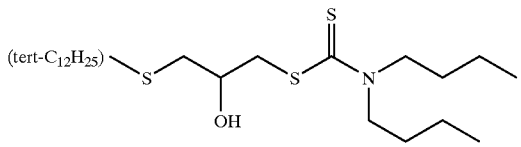

Inventive Example 2

A 2000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (138.9 g, 1.50 mol) and 2-ethylhexyl 3-mercaptopropionate (327.6 g, 1.50 mol). The mixture is stirred with cooling to approximately 5°–10° C. Sodium hydroxide (63.0 g, 1.58 mol), water (700 g) and tetrabutylammonium hydroxide (40% in water, 18.8 g, 19 mmol) are combined with mixing and slowly added to the epichlorohydrin and 2-ethylhexyl 3-mercaptopropionate over a 1 hour period. An exotherm is observed at the beginning of the addition that causes the temperature to reach 80° C. The temperature is returned to 5° C. and cooling is continued maintaining the reaction temperature between 5°–10° C. for the remainder of the addition. After the addition the reaction is heated for 2 hours at 50° C. and cooled overnight. The following morning the reaction is cooled to 5° C. and carbon disulfide (120.0 g, 1.58 mol) is added. Next, dibutylamine (193.8.0 g, 1.50 mol) is slowly added over 1 hour while maintaining the reaction temperature between 5°–15° C. The reaction is heated at 80° C. for 1 hour and then 5.0 g of 30% hydrogen peroxide is added at 70° C. The reaction is heated at 70° C. for an additional 15 minutes, cooled to 50° C., and the phases separated. The organic portion is washed with 400 mL of 10% aqueous sodium bicarbonate. Toluene (300 mL) is added to improve phase separation and the organic solution is washed with 2×300 mL of water. Toluene is removed on a rotary evaporator under a water aspirator vacuum. The organic product is then returned to a 1000 mL three neck round bottom flask and residual water is removed under vacuum at 60° C. for 3 hours. The product is filtered through a coarse fritted glass funnel yielding 692.0 g (95.2%) of a clear yellow viscous liquid with the following physical and chemical properties:

| | |
|---|---|
| Nitrogen Content | 3.00 wt % |
| Sulfur Content | 19.28 wt % |
| Viscosity @ 40° C. | 116 cSt |
| Low Molecular Weight GPC Analysis | 91.3% dialkylated product (r.t. = 22.6 min) |
| TGA Weight Loss | 10% loss @ 236° C. |
| | 25% loss @ 269° C. |
| | 50% loss @ 288° C. |

FT-IR, $^{13}$C-NMR and H-NMR analysis confirms that the main component of the mixture is 2-ethylhexyl 3-[[3-[[(dibutylamino)thioxomethyl]thio]-2-hydroxypropyl]thio]propanoate having the following chemical structure:

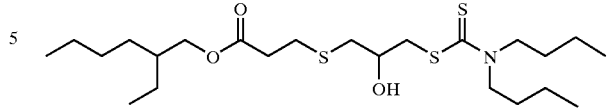

Inventive Example 3

A 1000 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (46.3 g, 0.50 mol) and n-dodecylmercaptan (101.2 g, 0.50 mol). The mixture is stirred with cooling to approximately 5°–10° C. Sodium hydroxide (21.0 g, 0.52 mol), water (240 g) and tetrabutylammonium hydroxide (40% in water, 7.0 g, 7 mmol) are combined with mixing and slowly added to the epichlorohydrin and n-dodecylmercaptan over a 1 hour period. An exotherm is observed and cooling is continued maintaining the reaction temperature between 5°–10° C. during the addition. After the addition the reaction is heated for 2 hours at 50° C. and cooled to 5° C. Carbon disulfide (40.0 g, 0.53 mol) is then added rapidly to the reaction mixture. Next, dibutylamine (64.6 g, 0.50 mol) is slowly added over 1 hour while maintaining the reaction temperature between 5°–15° C. After the addition the reaction is heated at 80° C. for 1 hour and then 1.0 g of 30% hydrogen peroxide is added at 80° C. The reaction is heated at 80° C. for an additional 30 minutes, cooled to 50° C., and the phases separated. The organic portion is washed with 2×100 mL of water. The organic solution is returned to a 500 mL three neck round bottom flask and residual water is removed under vacuum at 60° C. for 2 hours. The product is filtered through a coarse fritted glass funnel yielding 226.6 g (97.7%) of a clear yellow viscous liquid with the following physical and chemical properties:

| | |
|---|---|
| Nitrogen Content | 3.10 wt % |
| Sulfur Content | 19.21 wt % |
| Viscosity @ 40° C. | 85 cSt |
| Low Molecular Weight GPC Analysis | 96.8% dialkylated product (r.t. = 22.3 min) |
| TGA Weight Loss | 10% loss @ 228° C. |
| | 25% loss @ 267° C. |
| | 50% loss @ 287° C. |

FT-IR, $^{13}$C-NMR and H-NMR analysis confirms that the main component of the mixture is the 3-(n-dodecylthio)-2-hydroxypropyl dibutylcarbamodithioate having the following chemical structure:

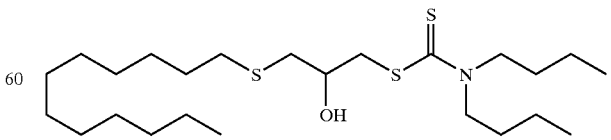

Inventive Example 4

A 250 mL four neck round bottom flask is equipped with a mechanical stirrer, an addition funnel, a thermometer, and a reflux condenser cooled to approximately 5° C. Dry nitrogen is passed into the reactor through the addition funnel and out of the reactor through the reflux condenser. The reactor is chilled with an ice water bath and charged with epichlorohydrin (11.6 g, 0.125 mol) and tert-dodecylmercaptan (25.3 g, 0.125 mol). The mixture is stirred with cooling to approximately 5°–10° C. Sodium hydroxide (5.2 g, 0.13 mol), water (60 mL) and tetrabutylammonium hydroxide (40% in water, 1.75 g, 1.7 mmol) are combined with mixing and slowly added to the epichlorohydrin and tert-dodecylmercaptan over a 1 hour period. An exotherm is observed and cooling is continued maintaining the reaction temperature between 5°–10° C. during the addition. After the addition the reaction mixture is slowly warmed to room temperature over 1½ hours. The reaction is heated for an additional 1 hour at 50° C. and then cooled to 5° C. Carbon disulfide (10.0 g, 0.131 mol) is added rapidly to the reaction mixture. Then bis(2-ethylhexyl)amine (30.3 g, 0.125 mol) is slowly added over 1 hour while maintaining the reaction temperature between 5°–15° C. The reaction is heated at 80° C. for 1 hour and diluted with 60 mL of toluene. The phases are separated and the organic portion is washed with 50 mL of water. The organic solution is dried with MgSO$_4$ and concentrated on a rotary evaporator for 2 hours. A yellow viscous liquid (69.9 g, 96.7%) is isolated. Sulfur content=15.26 wt %, Nitrogen content=2.66 wt %. Low molecular weight GPC analysis of the liquid shows the presence of a main peak (90.7%. r. t.=22.1 min) corresponding to a product formed by dialkylating epichlorohydrin. FT-IR, $^{13}$C-NMR and H-NMR analysis confirms that the main component of the mixture is 3-(tert-dodecylthio)-2-hydroxypropyl bis(2-ethylhexyl)carbamodithioate having the following chemical structure.

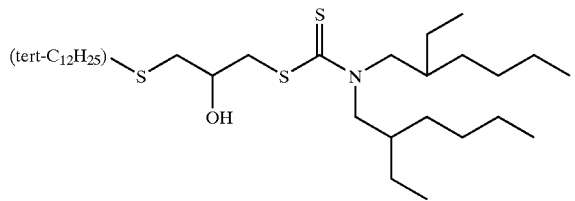

Inventive Example 5

In a procedure analogous to that followed in Inventive Example 4, 2-ethylhexylamine is reacted with tert-dodecylmercaptan, epichlorohydrin, and carbon disulfide. A yellow viscous liquid (56.2 g, 96.6%) is isolated. Sulfur content=19.43 wt %, Nitrogen content=3.37 wt %. Low molecular weight GPC analysis of the liquid shows the presence of a main peak (79.9%, r. t.–22.5 min) corresponding to a product formed by dialkylating epichlorohydrin. FT-IR, $^{13}$C-NMR and H-NMR analysis confirms that the main component of the mixture is 3-(tert-dodecylthio)-2-hydroxypropyl 2-ethylhexylcarbamodithioate having the following chemical structure:

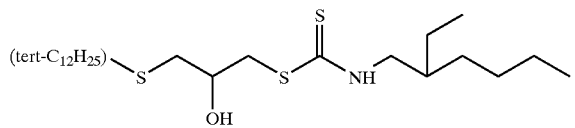

The advantages of the new alkylthio- and hydroxyl-substituted dithiocarbamates are shown in the following examples where their effectiveness as antioxidants, friction modifiers and anti-wear additives is demonstrated. In Example 6, the benefits as antioxidants over alkoxy- and hydroxyl-substituted dithiocarbamates is demonstrated. In Example 7, the benefits as friction modifiers over a commercial dithiocarbamate Vanlube 7723 (DTC) and zinc dialkyldithiophosphates (ZDDP) are demonstrated. In Example 8, the benefits as wear inhibitors over DTC are demonstrated. In Example 9, the benefits as wear inhibitors in the presence of a wear promoter are demonstrated. In Example 10, TGA is used to explain the observed performance properties.

Example 6

A variety of alkylthio- and hydroxyl-substituted dithiocarbamates and alkoxy- and hydroxyl-substituted dithiocarbamates were blended into an SAE Grade 5W-30 type motor oil as shown in Table 1. These oils contained a typical dispersant inhibitor package and were formulated with a low sulfur and low aromatic hydrocracked and isodewaxed basestock that meets the API Group II category. The oils contained 500 ppm phosphorus derived from secondary zinc dialkyldithiophosphate (ZDDP). For comparison, a commercial dithiocarbamate antioxidant (DTC), Vanlube 7723, available from R.T. Vanderbilt company, Inc., a commercial sulfurized olefin antioxidant (SO), HiTEC 7188, available from Ethyl Corporation, and a commercial zinc dialkyldithiophosphate (ZDDP), HiTEC 7169 available from Ethyl Corporation, were included in the study. All additive treat rates for the dithiocarbamates, sulfurized olefin and the zinc dialkyldithiophosphate were based on delivering equal sulfur to the oil (1500 ppm sulfur). Therefore, the higher the sulfur content is of the additive, the lower the additive treat rate to the finished oil is. It is desirable to have low additive treat rates. Some oils also contained an alkylated diphenylamine antioxidant (DPA), HiTEC 4793, available from Ethyl Corporation. The oxidation stability of these oils was measured by pressurized differential scanning calorimetry (PDSC) as described by J. A. Walker and W. Tsang in "Characterization of Lubrication Oils By Differential Scanning Calorimetry", SAE Technical Paper Series, 801383 (Oct. 20–23, 1980). Oil samples were treated with an iron (III) naphthenate catalyst (55 ppm Fe) and 2.0 milligrams were analyzed in an open aluminum hermetic pan. The DSC cell was pressurized with 500 psi air and programmed with the following heating sequence: (1) jump from ambient to 155° C., (2) ramp from 155° C. to 175° C. at 10° C./minute, (3) ramp from 175° C. to 185° C. at 5° C./minute, (4) iso-track at 185° C. The oil samples were held at 185° C. until an exothermic release of heat was observed. The exothermic release of heat marks the oxidation reaction. The time from the start of the experiment to the exothermic release of heat is called the oxidation induction time and is a measure of the oxidative stability of the oil (i.e. the longer the oxidation induction time, the greater the oxidative stability of the oil). All oils are evaluated in duplicate and the results averaged. As shown in Table 1, at an equal sulfur comparison the new alkylthio- and hydroxyl-substituted dithiocarbamates are more effective than alkoxy- and hydroxyl-substituted dithiocarbamates.

TABLE 1

| Oil ID | 5W-30 Motor Oil (wt. %) | DPA (wt. %) | Additive | Additive Treat (wt. %) | 100 N Diluent (wt. %) | Induction Time (min) |
|---|---|---|---|---|---|---|
| 1 | 97.506 | 0.00 | None | 0.00 | 2.494 | 14.4 |
| 2 | 97.506 | 0.50 | None | 0.00 | 1.994 | 43.8 |
| 3 | 97.506 | 0.50 | SO | 1.20 | 0.794 | 77.9 |
| 4 | 97.506 | 0.50 | Comparative Example 1 | 1.21 | 0.784 | 49.6 |
| 5 | 97.506 | 0.50 | Comparative Example 2 | 0.93 | 1.064 | 66.6 |
| 6 | 97.506 | 0.50 | Inventive Example 1 | 0.74 | 1.254 | 80.3 |
| 7 | 97.506 | 0.50 | Inventive Example 2 | 0.77 | 1.224 | 89.4 |
| 8 | 97.506 | 0.50 | Inventive Example 3 | 0.75 | 1.244 | 86.8 |
| 9 | 97.506 | 0.50 | ZDDP | 0.60 | 1.894 | 83.7 |
| 10 | 97.506 | 0.50 | DTC | 0.50 | 1.494 | 98.3 |

Example 7

The same oils evaluated for oxidation performance in Example 6 were also evaluated for boundary friction properties using the High Frequency Reciprocating Rig (HFRR). In this instrument 1–2 milliliters of the test motor oil are placed in a temperature controlled steel pan. A steel ball attached to a moveable arm is lowered into the pan. A load of 400 grams is applied to the steel ball/arm assembly. The steel/ball arm assembly is oscillated at 20 Hz over a 1 millimeter path length. As the arm is oscillated a friction coefficient is determined every 5 seconds. The test lasts 3 minutes so approximately 30 data points are averaged to determine the friction coefficient of an oil. A reduction in the friction coefficient corresponds to improved friction properties of the oil. Duplicate tests were formed on each oil at 130° C. The average friction coefficient for each sample is shown in Table 2. The results show that the addition of zinc dialkyldithiophosphate (ZDDP), or methylenebis (dibutyldithiocarbamate) (DTC) is detrimental to the friction properties of the oil. However, the alkylthio- and hydroxyl-substituted dithiocarbamates and the alkoxy- and hydroxyl-substituted dithiocarbamates show no harm to the friction properties of the oil.

formulated with a low sulfur and low aromatic hydrocracked and isodewaxed basestock that meets the API Group II category. The oils also contained 500 ppm phosphorus derived from secondary zinc dialkyldithiophosphate (ZDDP) and 0.3 wt. % HiTEC 4793 alkylated diphenylamine antioxidant. For comparison, a commercial dithiocarbamate antioxidant (DTC), Vanlube 7723, was included in the study. All additive treat rates for the dithiocarbamates were based on delivering equal sulfur to the oil (750 ppm sulfur). Therefore, the higher the sulfur content of the additive, the lower the additive treat rate to the finished oil. All oils were treated with 1.0 wt. % cumene hydroperoxide as a wear promoter prior to testing. Results in the Four Ball Wear Test are reported as a wear scar in millimeters. Low values for wear scar indicate effective wear protection while high values indicate poor wear protection. The results in Table 3 clearly show that the addition of the alkylthio- and hydroxyl-substituted dithiocarbamates reduces the wear scar in the Four Ball Wear Test. The results also show that the new alkylthio- and hydroxyl-substituted dithiocarbamates are more effective than the commercial dithiocarbamate Vanlube 7723 at reducing the wear scar.

TABLE 2

| Oil ID | 5W-30 Motor Oil (wt. %) | DPA (wt. %) | Additive | Additive Treat (wt. %) | 100 N Diluent (wt. %) | Friction Coefficient |
|---|---|---|---|---|---|---|
| 1 | 97.506 | 0.00 | None | 0.00 | 2.494 | 0.083 |
| 2 | 97.506 | 0.50 | None | 0.00 | 1.994 | 0.075 |
| 3 | 97.506 | 0.50 | SO | 1.20 | 0.794 | 0.081 |
| 4 | 97.506 | 0.50 | Comparative Example 1 | 1.21 | 0.784 | 0.077 |
| 5 | 97.506 | 0.50 | Comparative Example 2 | 0.93 | 1.064 | 0.075 |
| 6 | 97.506 | 0.50 | Inventive Example 1 | 0.74 | 1.254 | 0.074 |
| 7 | 97.506 | 0.50 | Inventive Example 2 | 0.77 | 1.224 | 0.076 |
| 8 | 97.506 | 0.50 | Inventive Example 3 | 0.75 | 1.244 | 0.075 |
| 9 | 97.506 | 0.50 | ZDDP | 0.60 | 1.894 | 0.086 |
| 10 | 97.506 | 0.50 | DTC | 0.50 | 1.494 | 0.085 |

Example 8

The anti-wear properties of the alkylthio- and hydroxyl-substituted dithiocarbamates were demonstrated using the Four Ball Wear Test as defined in ASTM D-4172. The additives being evaluated were blended into a SAE Grade 5W-30 type motor oil as shown in Table 3. The motor oils contained a typical dispersant inhibitor package and were

TABLE 3

| Oil ID | 5W-30 Motor Oil (wt. %) | Additive | Additive Treat (wt. %) | 100 N Diluent (wt. %) | Wear Scar (mm) |
|---|---|---|---|---|---|
| 11 | 98.1 | None | 0.00 | 1.90 | 0.73 |
| 12 | 98.1 | Inventive Example 1 | 0.37 | 1.53 | 0.54 |

TABLE 3-continued

| Oil ID | 5W-30 Motor Oil (wt. %) | Additive | Additive Treat (wt. %) | 100 N Diluent (wt. %) | Wear Scar (mm) |
|---|---|---|---|---|---|
| 13 | 98.1 | Inventive Example 2 | 0.38 | 1.52 | 0.60 |
| 14 | 98.1 | Inventive Example 3 | 0.38 | 1.52 | 0.52 |
| 15 | 98.1 | DTC | 0.25 | 1.65 | 0.63 |
| 16 | 98.1 | Sulfurized Olefin | 0.38 | 1.53 | 0.63 |

Example 9

Four Ball Wear Tests, as defined above, were performed in a slightly different motor oil. The additives being evaluated were blended into an SAE Grade 5W-30 type motor oil as shown in Table 4. The motor oils contained a typical dispersant inhibitor package and were formulated with a low sulfur and low aromatic hydrocracked and isodewaxed basestock that meets the API Group II category. The oils also contained 500 ppm phosphorus derived from secondary zinc dialkyldithiophosphate (ZDDP) and 0.4 wt. % HiTEC 4793 alkylated diphenylamine antioxidant. In these evaluations varying levels of cumene hydroperoxide (peroxide) were used. The dithiocarbamate treat rates were based on delivering approximately 1500 ppm sulfur to the finished motor oil. The results in Table 4 clearly show that in the presence of the wear promoter, the addition of the alkylthio- and hydroxyl-substituted dithiocarbamates of the present invention reduces the wear scar in the Four Ball Wear Test.

TABLE 4

| Oil ID | 5W-30 Motor Oil (wt. %) | Additive | Additive Treat (wt. %) | 100 N Diluent (wt. %) | Wear Scar No Peroxide (mm) | Wear Scar 0.50% Peroxide (mm) | Wear Scar 1% Peroxide (mm) |
|---|---|---|---|---|---|---|---|
| 17 | 99.2 | None | 0.00 | 0.80 | 0.427 | 0.607 | 0.740 |
| 18 | 99.2 | Inventive Example 1 | 0.80 | 0.00 | 0.434 | 0.526 | 0.600 |
| 19 | 99.2 | Inventive Example 2 | 0.80 | 0.00 | 0.453 | 0.539 | 0.600 |

Example 10

Thermal Gravimetric Analysis (TGA) can be used as a tool to qualitatively estimate the thermal stability of additives. This test involves heating a small sample of additive following a specific temperature ramping sequence. The TGA instrument monitors sample weight loss as a function of temperature. For materials with approximately the same molecular weight, a more rapid weight loss rate corresponds roughly to reduced thermal stability. TGAs were performed on the new alkylthio- and hydroxyl-substituted dithiocarbamates of the present invention and a commercial dithiocarbamate Vanlube 7723 (DTC). The following heating sequence was used: equilibrate at 30° C., ramp at 20° C./min to 900° C. The experiments were performed under a nitrogen atmosphere. The temperatures at which specific weight losses were observed are reported in Table 5. The results show that the alkylthio- and hydroxyl-substituted dithiocarbamates of the present invention are more volatile than the commercial dithiocarbamate DTC. Since the molecular weights of the new dithiocarbamates are slightly higher than DTC, the more rapid weight loss is due to reduced thermal stability. This data illustrates that the dithiocarbamates of the present invention are decomposing at lower temperatures than the conventional DTC, and such a property explains the improved anti-wear and friction performance of the new dithiocarbamates relative to conventional DTC.

TABLE 5

| | Dithiocarbamate Sample | | | |
|---|---|---|---|---|
| | Inventive Example 1 | Inventive Example 2 | Inventive Example 3 | DTC |
| Additive Molecular Weight Calcd. | 464 | 480 | 464 | 423 |
| TGA Weight Loss Temperature (C.) | | | | |
| 10% @ | 212 | 236 | 228 | 302 |
| 25% @ | 241 | 269 | 267 | 316 |
| 50% @ | 268 | 288 | 287 | 329 |

This invention is susceptible to considerable variation in its practice. Accordingly, this invention is not limited to the specific exemplifications set forth hereinabove. Rather, this invention is within the spirit and scope of the appended claims, including the equivalents thereof available as a matter of law.

The patentee does not intend to dedicate any disclosed embodiments to the public, and to the extent any disclosed modifications or alterations may not literally fall within the scope of the claims, they are considered to be part of the invention under the doctrine of equivalents.

What is claimed is:

1. A composition having the following chemical structure:

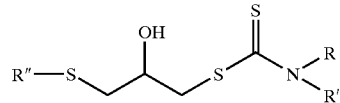

wherein R and R' may be hydrogen or alkyl, where at least one of R or R' is an alkyl group having at least three carbon atoms, where R" is alkyl, or R'" OCOCH$_2$, or R'" OCOCH$_2$CH$_2$, and where R'" is alkyl.

2. The composition of claim 1, wherein R and R' are independently selected from alkyl groups having at least three carbon atoms.

3. The composition of claim 1, wherein R" is R'" OCOCH$_2$.

4. The composition of claim 1, wherein R" is R'" OCOCH$_2$CH$_2$.

5. The composition of claim 1, wherein R" is an alkyl group.

6. The composition of claim 5, wherein R" is a C$_4$ to C$_{12}$ alkyl group.

7. The composition of claim 5, wherein R" is a C$_9$ to C$_{12}$ alkyl group.

8. The composition of claim 1, wherein R and R' are independently selected from alkyl groups having three to eight carbon atoms.

9. The composition of claim 1, wherein R and R' are independently selected from alkyl groups having four to six carbon atoms.

10. A method of preparing a composition comprising reacting an alkyl glycidyl thioether with a primary and/or secondary amine, and carbon disulfide.

11. The method of claim 10, wherein the composition is a lubricant additive.

12. A lubricant additive prepared by the method of claim 11.

13. The reaction product prepared by the method of claim 10.

14. A lubricating oil comprising the composition of claim 1 and a base oil of lubricating viscosity.

15. The lubricating oil of claim 14, further comprising at least one of a detergent, a dispersant, an antiwear agent, a friction modifier, a pour point depressant, a foam inhibitor, a corrosion inhibitor, a rust inhibitor, and a viscosity index improver.

16. A lubricating oil composition comprising the lubricant additive of claim 12, and a base oil of lubricating viscosity.

17. The lubricating oil of claim 14, further comprising at least one antioxidant selected from diphenylamines, phenothiazines, hindered phenols, sulfurized hindered phenols, alkyl phenols, sulfurized alkyl phenols, methylene-bridged hindered phenols, sulfides and polysulfides, sulfurized olefins, and sulfurized fats and oils.

18. A passenger car crankcase engine oil comprising the composition of claim 1.

19. A heavy duty diesel engine oil comprising the composition of claim 1.

20. A railroad oil comprising the composition of claim 1.

21. A natural gas engine oil comprising the composition of claim 1.

22. A hydraulic oil comprising the composition of claim 1.

23. A turbine oil comprising the composition of claim 1.

24. A rust and oxidation oil comprising the composition of claim 1.

25. An automatic transmission fluid comprising the composition of claim 1.

26. The composition of claim 1, wherein the total sum of carbon atoms in R, R' and R" is greater than ten.

27. The composition of claim 1, wherein R, R', R", and R'" are alkyl and are independently selected from linear and branched isomers.

28. The composition of claim 1, wherein R, R', R", and R'" are alkyl and are independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl, and isomers thereof.

29. The method of claim 10, wherein the alkyl glycidyl thioether, primary and/or secondary amine, and carbon disulfide are combined at approximately equal molar concentrations.

30. The method of claim 10, comprising the steps:
providing an epoxide by reacting a mercaptan and epichlorohydrin; and
reacting the epoxide with the amine and carbon disulfide.

31. The method of claim 30, wherein the epoxide is not isolated or purified before reacting with said amine and carbon disulfide.

32. The method of claim 10, wherein the epoxide is alkyl glycidyl thioether and the amine is a primary amine.

33. The method of claim 10, wherein the epoxide is alkyl glycidyl thioether and the amine is a secondary amine.

34. The method of claim 10, wherein the alkyl glycidyl thioether is selected from methylglycidyl thioether, ethylglycidyl thioether, n-propylglycidyl thioether, n-butylglycidyl thioether, sec-butylglycidyl thioether, n-hexylglycidyl thioether, cyclohexylglycidyl thioether, n-octylglycidyl thioether, tert-nonylglycidyl thioether, n-dodecylglycidyl thioether, tert-dodecylglycidyl thioether, and mixtures thereof.

35. The method of claim 10, wherein the alkyl glycidyl thioether is a carboxylic acid ester-substituted alkyl glycidyl thioether.

36. A composition having the following chemical structure:

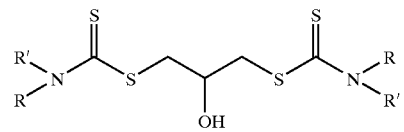

wherein R and R' are independently selected from alkyl groups having at least three carbon atoms.

37. The composition of claim 36, wherein R and R' are independently selected from alkyl groups having four to twenty-two carbon atoms.

38. The composition of claim 36, wherein R and R' are independently selected from alkyl groups having four to six carbon atoms.

39. A composition of 3-(tert-dodecylthio)-2-hydroxypropyl 2-ethylhexylcarbamodithioate.

40. A composition having the following chemical structure:

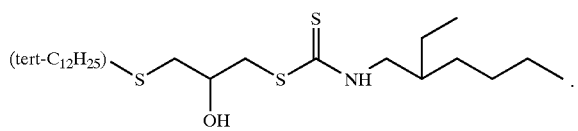

41. A composition of 3-(tert-dodecylthio)-2-hydroxypropyl dibutylcarbamodithioate.

42. A composition having the following chemical structure:

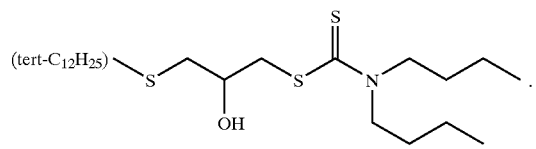

43. A composition of 2-ethylhexyl 3-[[3-[[(dibutylamino)thioxomethyl]thio]-2-hydroxypropyl]thio]propanoate.

44. A composition having the following chemical structure:

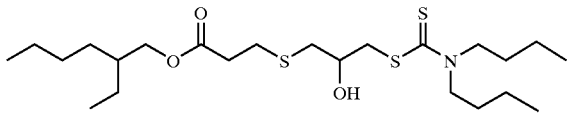

45. A composition of 3-(n-dodecylthio)-2-hydroxypropyl dibutylcarbamodithioate.

46. A composition having the following chemical structure:

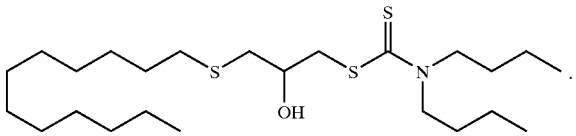

47. A composition of 3-(tert-dodecylthio)-2-hydroxypropyl bis(2-ethylhexyl)carbamodithioate.

48. A composition having the following chemical structure:

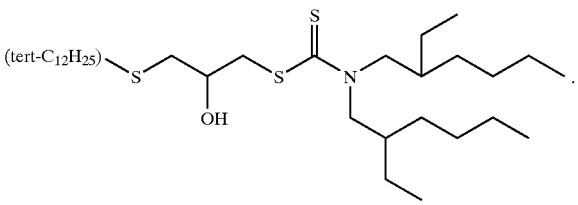

49. A method of reducing the oxidation of a lubricating oil comprising adding to an oil of lubricating viscosity an oxidation-reducing amount of a composition of claim 1.

50. A method of reducing the deposit formation in an engine lubricated with a lubricating oil, said method comprising adding to an oil of lubricating viscosity a deposit-reducing amount of a composition of claim 1, and lubricating an engine with said lubricating oil.

51. A method of reducing engine wear in an engine lubricated with a lubricating oil, said method comprising adding a wear-reducing amount of a composition of claim 1 to an oil of lubricating viscosity, and lubricating an engine with said oil.

52. A method of reducing engine friction in an engine lubricated with a lubricating oil, said method comprising adding a friction-reducing amount of a composition of claim 1 to an oil of lubricating viscosity, and lubricating an engine with said oil.

53. A method of improving fuel economy in an engine lubricated with a lubricating oil, said method comprising adding a fuel economy-improving amount of a composition of claim 1 to an oil of lubricating viscosity, and lubricating an engine with said oil.

54. The method of claim 49, further comprising lubricating an engine with said lubricating oil.

55. The method of claim 49, further comprising lubricating a gear with said lubricating oil.

56. The method of claim 49, further comprising lubricating an automatic transmission with said lubricating oil.

57. The method of claim 49, further comprising lubricating a hydraulic mechanism with said lubricating oil.

58. An engine lubricated with an oil comprising a composition of claim 1.

59. A gear lubricated with an oil comprising a composition of claim 1.

60. An automatic transmission lubricated with an oil comprising a composition of claim 1.

61. A turbine lubricated with an oil comprising a composition of claim 1.

62. The composition of claim 1, wherein R and R' are independently selected from alkyl groups having three to twenty-two carbon atoms.

63. A composition having the following chemical structure:

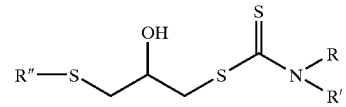

wherein R and R' may be hydrogen or alkyl, wherein at least one of R or R' is an alkyl group, where R" is R'"OCOCH$_2$ or R'"OCOCH$_2$CH$_2$, and where R'" is an alkyl group.

64. A composition having the following chemical structure:

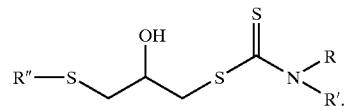

65. A composition having the following chemical structure:

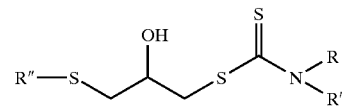

wherein R and R' are independently selected from alkyl groups having three to eight carbon atoms, where R" is alkyl, or R'"OCOCH$_2$ or R'"OCOCH$_2$CH$_2$, and where R'" is an alkyl group.

66. The composition of claim 65, wherein R and R' are independently selected from alkyl groups having four to six carbon atoms.

67. A composition having the following chemical structure:

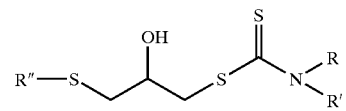

wherein R and R' may be hydrogen or alkyl, wherein at least one of R or R' is an alkyl group, where R" is alkyl, or R'"OCOCH$_2$ or R'"OCOCH$_2$CH$_2$, where R'" is alkyl, and wherein the total sum of carbon atoms in R, R' and R" is greater than ten.

* * * * *